United States Patent
Lim et al.

(10) Patent No.: US 10,900,963 B2
(45) Date of Patent: Jan. 26, 2021

(54) MULTI-DIAGNOSIS PARALLEL-TYPE LINEAR BIOCHIP

(71) Applicant: PROTEOMETECH INC., Seoul (KR)

(72) Inventors: Kook Jin Lim, Seoul (KR); Dong Seob Choi, Gyeonggi-do (KR); Bum Joon Kim, Seoul (KR); Mi Jung Kim, Seoul (KR); Myung Sook Chung, Seoul (KR); Hye Jung Lee, Incheon (KR)

(73) Assignee: PROTEOMETECH INC.

( * ) Notice: Subject to any disclaimer, the term of this patent is extended or adjusted under 35 U.S.C. 154(b) by 0 days.

(21) Appl. No.: 14/428,560

(22) PCT Filed: Jan. 15, 2014

(86) PCT No.: PCT/KR2014/000438
§ 371 (c)(1),
(2) Date: Mar. 16, 2015

(87) PCT Pub. No.: WO2014/137069
PCT Pub. Date: Sep. 12, 2014

(65) Prior Publication Data
US 2015/0362487 A1    Dec. 17, 2015

(30) Foreign Application Priority Data
Mar. 8, 2013    (KR) .................. 10-2013-0025216

(51) Int. Cl.
*G01N 33/545*    (2006.01)
*G01N 33/548*    (2006.01)
(Continued)

(52) U.S. Cl.
CPC ..... *G01N 33/54386* (2013.01); *G01N 33/545* (2013.01); *G01N 33/548* (2013.01); *G01N 33/552* (2013.01)

(58) Field of Classification Search
CPC ........... G01N 33/54386; G01N 33/545; G01N 33/548; G01N 33/552; G01N 33/48; G01N 33/5302; G01N 33/6803; C12Q 1/6813
See application file for complete search history.

(56) References Cited

U.S. PATENT DOCUMENTS 5,486,452 A * 1/1996 Gordon ............ G01N 33/54386
435/5
6,203,757 B1    3/2001 Lu et al.
(Continued)

FOREIGN PATENT DOCUMENTS

CN    101576562 A    11/2009
JP    2010261961 A    11/2010
(Continued)

OTHER PUBLICATIONS

Sartorius Stedim Biotech, UniSart 3D nitro slide for protein microarrays, UniSart 3D nitro slide for protein microarrays, (2012), vol. 04, URL, https://www.sartorius.com/fileadmin/fm-dam/sartorius_media/Lab-Products-and-Services/Diagnostics/Brochures/Broch_UniSart-3D_Nitro_Slide_SL-1527-e.pdf.
(Continued)

*Primary Examiner* — Gailene Gabel
(74) *Attorney, Agent, or Firm* — Riverside Law LLP

(57) ABSTRACT

The present invention is related to a parallel line biochip for multiplex diagnosis. The parallel line biochip for multiplex diagnosis includes a plurality of line strips disposed in parallel, and a well configured to immobilize the line strips. Since the parallel line biochip for multiplex diagnosis can be used to connect two or more line strips in parallel, the parallel line biochip for multiplex diagnosis has an effect of measuring various materials present in a biological test sample at the same time.

5 Claims, 3 Drawing Sheets

(51) Int. Cl.
*G01N 33/552* (2006.01)
*G01N 33/48* (2006.01)
*G01N 33/543* (2006.01)

(56) References Cited

U.S. PATENT DOCUMENTS

| | | | |
|---|---|---|---|
| 7,267,799 B1* | 9/2007 | Borich | G01N 21/8483 235/462.11 |
| 7,659,107 B2 | 2/2010 | Smith et al. | |
| 2004/0096985 A1 | 5/2004 | Kenjyou et al. | |
| 2007/0128072 A1* | 6/2007 | Lee | G01N 21/8483 422/400 |
| 2009/0124513 A1 | 5/2009 | Berg et al. | |
| 2010/0041571 A1 | 2/2010 | Cohen et al. | |
| 2011/0144535 A1* | 6/2011 | Guirguis | A61B 10/0051 600/573 |

FOREIGN PATENT DOCUMENTS

| | | |
|---|---|---|
| KR | 1020030089530 A | 11/2003 |
| WO | WO 02/24337 | 3/2002 |
| WO | 03029822 A1 | 4/2003 |
| WO | WO 2010/022913 | 3/2010 |
| WO | WO 2011/032278 | 3/2011 |

OTHER PUBLICATIONS

Miller et al., 1984, "Application of the MAST" Immunodiagnostic System to the Determination of Allergen-Specific IgE, Clinical Chemistry, vol. 30, No. 9, pp. 1467-1742, URL, http://www.clinchem.org/content/30/9/1467.full.pdf.

Dyk et al., 2008, "A high-throughput protein array-based approach for allergy screening & multiple parallel discovery & characterisation of IgE-binding proteins, a high-throughput protein array-based approach for allergy screening & multiple parallel discovery & characterisation of IgE-binding proteins," vol. 4, No. 24, URL, http://mms.technologynetworks.net/posters/0497.pdf.

Han et al., "Microfluidic Chips for Immunassays", Annual Review of Analytical Chemistry, 6(1): 119-141, 2013.

Dittrich et al., "Research Highlights", Lab Chip, 7(2): 161-163, 2007.

* cited by examiner

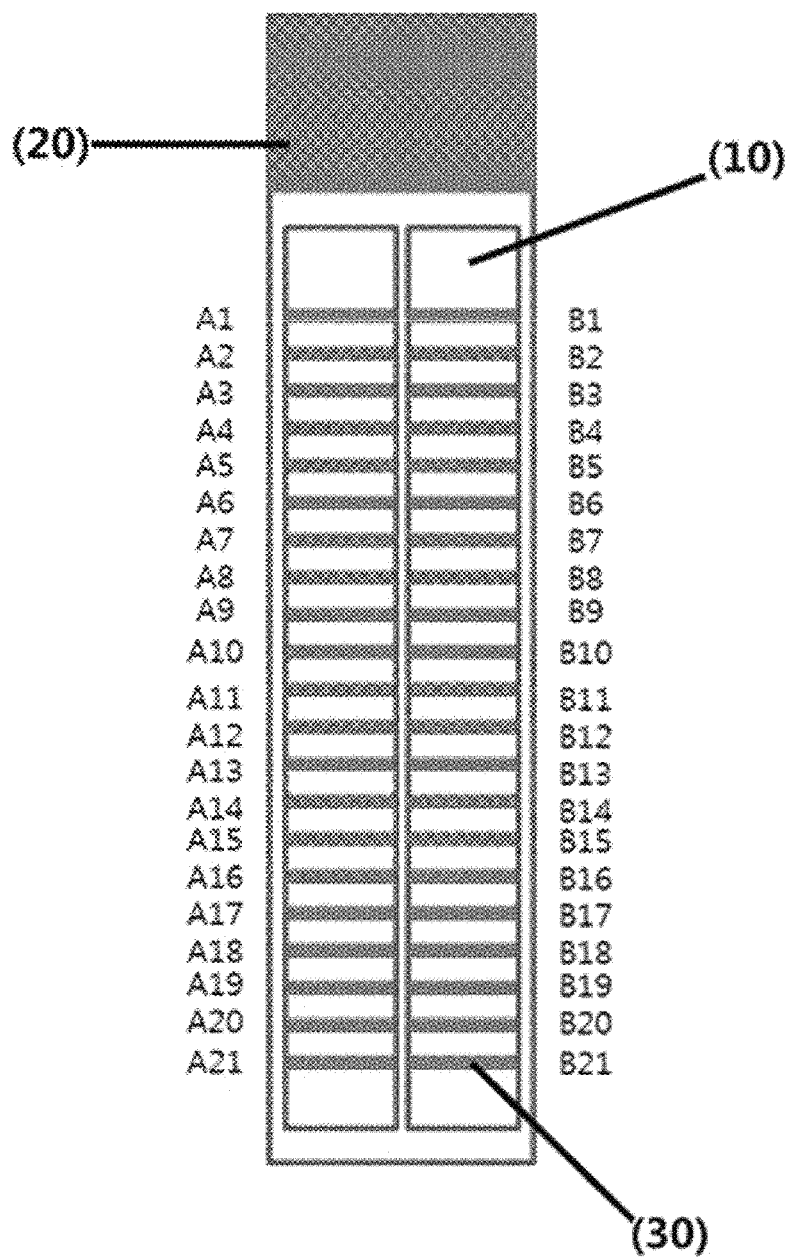
[Fig. 1]

[Fig 2]
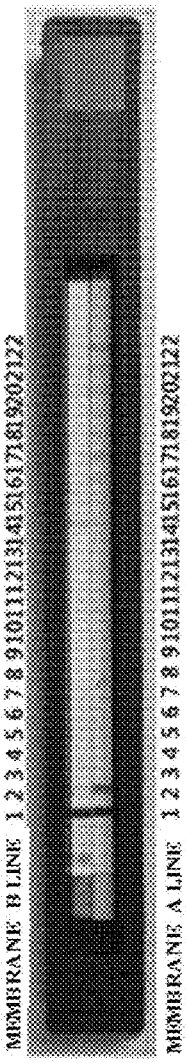

[Fig 3]
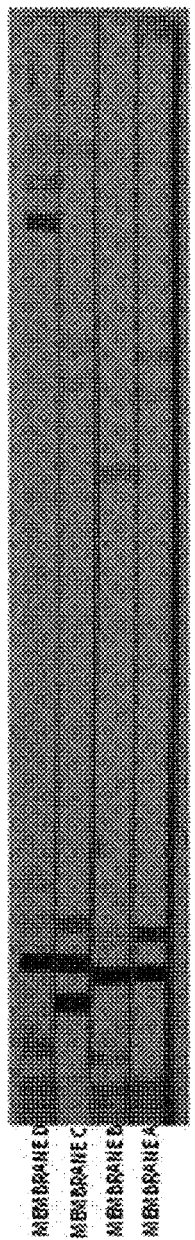

MULTI-DIAGNOSIS PARALLEL-TYPE LINEAR BIOCHIP

CROSS-REFERENCE TO RELATED APPLICATIONS

This application is the U.S. national phase application filed under 35 U.S.C. § 371 claiming benefit to International Patent Application No. PCT/KR2014/000438, filed on Jan. 15, 2014, which is entitled to priority under 35 U.S.C. § 119(a)-(d) to Korea application no. 10-2013-0025216, filed Mar. 8, 2013, each of which application is hereby incorporated herein by reference in its entirety.

TECHNICAL FIELD

The present invention relates to a parallel line biochip for multiplex diagnosis capable of analyzing various elements at once. More particularly, the present invention relates to a parallel line biochip for multiplex diagnosis, and a diagnostic kit and a diagnostic method using the same.

BACKGROUND ART

A biochip is a material used to obtain biological information, for example, confirming expression patterns of genes, and characterizing and quantifying proteins by immobilizing biological materials such as DNA, proteins, antibodies and the like in a solid substrate such as glass, silicone, a plastic, a metal, nitrocellulose, PVDF and the like and analyzing a reaction with a trace of a test sample. A protein chip has been used as a tool for characterizing and quantifying a certain protein in a test sample or analyzing biological functions of the certain protein by immobilizing a protein such as an antigen or an antibody reacting with the certain protein, followed by determining binding of the certain protein in a diagnostic test sample by means of a diagnostic method using absorbance, fluorescence, SPR, and the like.

Biochips may be divided into dot-type biochips and line-type biochips. Here, the dot-type biochips may be obtained by coating plates on many kinds of markers such as a DNA micro array, but they have a problem in that the plates should be coated one by one from the very beginning. The line-type biochips have advantages in that a production process is simple and mass production is possible since they are generally used in the form of strips obtained by horizontally drawing several lines of markers to be measured on a long membrane in the form of lines and vertically cutting the long membrane. Among line-type multiplex diagnostic kits, a kit for sequencing a nucleic acid sequence includes a commercially available kit capable of detecting HIV, mycobacteria, and the like.

A line strip kit for measuring a protein has been widely used in autoimmune antibodies, reagents for diagnosing allergies, and the like. An allergy is a hypersensitive immune response which is caused as IgE antibodies against a certain external substance are formed in the body. In this case, allergic diseases are diagnosed by quantifying a blood concentration of the IgE antibodies binding with allergens which can cause allergies. Since there are significant regional differences in distribution of allergens and the distribution of allergens is highly affected by food culture, several tens of allergens should be tested at the same time. Therefore, a test kit using a protein chip capable of diagnosing various species of allergens at the same time rather than performing individual tests on respective allergens has been used as an important test method. A commercially available diagnostic kit for diagnosing an allergy is used to immobilize 1 to 21 allergens in a nitrocellulose membrane, allowing the allergens to react with a serum and analyze specific bound IgE using fluorescence or absorbance. In this regard, Korean Patent Publication No. 2003-0089530 discloses a kit for diagnosing asthma or rhinitis, which includes cytokeratin 18 proteins. However, the kit has a problem in that the cytokeratin 18 proteins can only be diagnosed one by one.

However, the line strip kit has problems in that it is difficult to perform a test on a strip since the strip becomes long when many lines are put thereon, and that it may be difficult to analyze various elements when detection is performed once since the strip is composed of up to approximately 20 marker lines.

DISCLOSURE

Technical Problem

Therefore, to solve the problems of the prior art, the present inventors have endeavored to develop a diagnostic kit capable of analyzing various elements, and developed a technique of disposing line strips in parallel to design a diagnostic kit so that the diagnostic kit can measure many more kinds of substances all at once.

Therefore, the present invention is directed to a biochip for multiplex diagnosis including parallel line strips, and a multiplex diagnostic kit and a diagnostic method using the same.

However, the problems to be solved according to the present invention are not limited to the above-described problems, and other problems which are not disclosed herein may be made apparent to those skilled in the art from the detailed description provided below.

Technical Solution

According to an aspect of the present invention, there is provided a parallel line biochip for multiplex diagnosis including line strips disposed in parallel.

According to one exemplary embodiment of the present invention, the biochip is characterized in that it includes a plurality of line strips disposed in parallel, and a well configured to immobilize the line strips.

According to another exemplary embodiment of the present invention, the line strips are characterized in that they are prepared by coating a membrane onto a support.

According to still another exemplary embodiment of the present invention, the membrane is characterized in that it includes a marker.

According to still another exemplary embodiment of the present invention, the membrane is characterized in that it is selected from the group consisting of nitrocellulose, nylon, polyvinylidene fluoride (PVDF), glass, and a plastic.

According to yet another exemplary embodiment of the present invention, the marker is characterized in that it is selected from the group consisting of a protein, an antigen, an antibody, DNA, RNA, PNA, a drug, a chemical substance, and an aptamer.

According to another aspect of the present invention, there is provided a diagnostic method using the parallel line biochip for multiplex diagnosis according to the present invention, which includes allowing a biological test sample to come in contact with a marker to measure a concentration of a material present in the biological test sample.

According to one exemplary embodiment of the present invention, the marker is characterized in that it is selected from the group consisting of a protein, an antigen, an antibody, DNA, RNA, PNA, a drug, a chemical substance, and an aptamer.

According to another exemplary embodiment of the present invention, the biological test sample is characterized in that it is selected from the group consisting of tissues, cells, whole blood, serum, plasma, saliva, cerebrospinal fluid, and urine.

According to still another exemplary embodiment of the present invention, the material is characterized in that it is selected from the group consisting of immunoglobulin E (IgE), an autoantibody, a cytokine, a protein, a drug, a chemical substance, DNA, and RNA.

According to still another aspect of the present invention, there is provided a reader for evaluating a parallel-line diagnostic kit for multiplex diagnosis.

Advantageous Effects

Since a conventional line strip biochip used strips obtained by immobilizing 2 to 21 materials in the form of lines, it used respective line strips in a number of reaction wells when there were many materials to be analyzed. Therefore, the conventional line strip biochip has problems in that a large amount of a specimen is consumed, and a cycle of processes including introducing respective reaction solutions for biochips, allowing the biochips to react with materials and washing the biochips should be repeatedly performed.

However, a parallel line biochip for multiplex diagnosis provided in the present invention has an advantage in that 40 or more materials may be analyzed since one parallel strip is prepared by minimizing individual line strips, disposing the plurality of line strips in parallel.

DESCRIPTION OF DRAWINGS

These and other features, aspects, and advantages of preferred embodiments of the present invention will be more fully described in the following detailed description, taken accompanying drawings. In the drawings:

FIG. 1 is a schematic view showing a parallel line biochip according to the present invention;

FIG. 2 shows a two-strip parallel line biochip prepared by attaching two line strips; and FIG. 3 shows a four-strip parallel line biochip prepared by attaching four line strips.

BEST MODE

The present invention is directed to a biochip capable of diagnosing many kinds of biomarkers at the same time by disposing line strips in parallel.

The present inventors have conducted research on a biochip in the form of line strips as a plan to improve the efficiency of a conventional biochip in which the line strips are long and which requires a large amount of a specimen when many kinds of markers are included on the line strips, and proposed that the many kinds of markers may be measured all at once since the line strips are disposed in parallel so that the plurality of line strips can be included in one biochip. Therefore, the present invention has been completed based on these facts.

Therefore, the present invention is directed to a parallel line biochip in which line strips are disposed in parallel.

The parallel line biochip in which line strips are disposed in parallel according to the present invention is characterized in that it includes a plurality of line strips disposed in parallel, and a well configured to immobilize the line strips.

The line strips (10) are disposed in parallel in one biochip, and the well (20) capable of immobilizing the line strips is included in the one biochip (see FIG. 1).

Conventional line strips have a problem in that it is impossible to dispose the line strips since the line strips are long in a transverse direction, and thus materials may be detected only when the line strips are long in a longitudinal direction. However, the above problems can be solved in the present invention by manufacturing line strips so that the line strips are short in a transverse direction and attaching the plurality of line strips in parallel. In this case, the horizontal length of the line strips may be in a range of 0.1 mm to 100 mm, preferably 0.2 mm to 50 mm, and most preferably 0.5 mm to 25 mm.

Therefore, the parallel line biochip for multiplex diagnosis according to the present invention can be useful in detecting a wide range of materials in a small amount of a test sample, compared with the biochip in which line strips are lengthened in series, by disposing the line strips in parallel, and cutting a time required to detect the wide range of materials.

Also, since the line strip biochip is used instead of the dot-type biochip which has been used to detect various materials known in the related art, time and manpower required to draw lines of a marker on a membrane may be significantly reduced, which makes it possible to mass-produce the line strip biochip.

According to one exemplary embodiment of the present invention, each of the line strips includes a support. In this case, a membrane is coated on the support. Here, the membrane may be nitrocellulose, nylon, polyvinylidene fluoride (PVDF), glass, or a plastic, but is not limited as long as it can include a marker. The biochip according to the present invention is characterized in that two line strips are connected in parallel, as shown in FIG. 1.

In the present invention, the term "line strip" refers to a strip prepared by attaching a marker onto a membrane in the form of lines, and the expression "drawing lines" means that a marker is attached onto a membrane.

Also, a diagnostic method using the biochip according to the present invention may be provided. In this case, the concentration of a material to be expressed is measured by allowing a biological test sample to come in contact with the marker (30). The marker may be detected in contact with the biological test sample. In this case, a level of concentration of the material to be expressed is measured through comparison with that of a control. Here, the material may be an organic or inorganic material selected from the group consisting of a protein, an antigen, an antibody, DNA, RNA, PNA, a drug, a chemical substance, and an aptamer, but the present invention is not limited thereto. Also, the biological test sample may be tissues, cells, whole blood, serum, plasma, saliva, cerebrospinal fluid, or urine, but the present invention is not limited thereto.

The material to be expressed may be immunoglobulin E (IgE), an autoantibody, a cytokine, a protein, a drug, a chemical substance, DNA, or RNA. The concentration of the material to be expressed may be measured using a method of measuring fluorescence, absorbance, luminescence, magnetism, electric current flow, and the like.

The biochip provided in the present invention may be especially used as a protein chip for diagnosing an allergy, but the present invention is not limited thereto. For example, biochips in which line strips are disposed in parallel may be used without limitation.

An allergy is a hypersensitive immune response which is caused as immunoglobulin E (IgE) antibodies against a certain external substance are formed in the body.

In diagnosis of an allergy, it is very important to simultaneously detect various allergens which can cause an allergy. Therefore, when the biochip according to the present invention is used, a number of allergens can be detected at the same time.

Also, the present invention provides a reader for evaluating a parallel line biochip for multiplex diagnosis. The reader can be useful in automatically determining whether a protein is expressed in response to any materials by recognizing an expression level of the protein in the biochip.

Hereinafter, preferred exemplary embodiments of the present invention will be described in order to aid in understanding the present invention. However, it should be understood that the description set forth herein is merely exemplary and illustrative of exemplary embodiments for the purpose of describing the present invention, and is not intended to limit the present invention.

EXAMPLES

Example 1

Manufacture of Biochip Using Parallel Line Strips

100 μl of a Sulfo NHS-LC-LC-biotin solution obtained by dissolving Sulfo NHS-LC-LC-biotin (Thermo, USA) in DMSO at a concentration of 5 mg/ml was slowly added to a bovine serum albumin (BSA) solution obtained by dissolving BSA in PBS at a concentration of 4 mg/ml. The resulting mixture was shielded with foil, and kept overnight at 4° C. for reaction. The reaction mixture was dialyzed twice overnight at 4° C. to prepare biotin-labeled BSA. A diluted biotin-labeled BSA solution was divided into 25 nitrocellulose (NC) membranes cut with a width of 5 cm and a length of 16 cm. The NC membranes coated with the biotin-labeled BSA in a transverse direction were dried overnight at room temperature in a dry chamber. Each of the dried NC membranes was attached to a plastic support, and cut at a distance of 1.5 mm in a longitudinal direction, and two of the cut NC membrane pieces were immobilized in each rectangular plastic reaction well using a double-sided adhesive tape. 0.4 ml of a PBS solution containing 0.5% BSA was put into the membrane-coated plastic reaction wells, and agitated for an hour. The solution in the reaction wells was discarded, and 0.4 ml of a streptavidin-alkaline phosphatase (streptavidin-AP; Promega, USA) solution was put into the reaction wells, and agitated for 30 minutes. The streptavidin-AP solution was discarded, and 0.4 ml of a washing solution (50 mm Tris, 0.2 M NaCl, 0.05% Tween 20) was divided into the reaction wells, and agitated at room temperature for 5 minutes. Then, the solution was removed. This procedure was additionally performed twice to completely remove unattached streptavidin-AP. 400 μl of a colorimetric solution containing 0.2 mg/ml of bromochlorophenyl phosphate and 0.3 mg/ml of nitroblue tetrazolium was put into the specimen-containing reaction wells, and agitated at room temperature to perform a colorimetric reaction. After 20 minutes, the solution was removed, and the reaction wells were washed with 400 μl of distilled water. Then, the remaining solution was removed, and the reaction wells were then dried.

As a result, it was confirmed that the strips were manufactured to be thin in a transverse direction so that the strips were able to be disposed in parallel. As shown in FIG. 2, it could be seen that colors were uniformly observed in the strips attached in parallel in the plastic reaction wells.

Example 2

Biochip-Attached Marker

As listed in Table 1, lines were drawn on two NC membranes (A and B) using 43 solutions, in which different allergens and proteins were dissolved, in the same manner as in Example 1, and the allergens were immobilized in the NC membranes. The NC membranes in which the allergens were immobilized were dried overnight at room temperature in a drying rack, and then attached to a plastic support. The NC membranes were cut at a distance of 1.5 mm in a longitudinal direction to manufacture strips. One strip manufactured on the membrane A and one strip manufactured on the membrane B were attached side by side to the inside of one plastic reaction well.

TABLE 1

| Membrane A | | Membrane B | |
|---|---|---|---|
| Line | Marker | Line | Marker |
| 1 | Biotin-BSA | 1 | Biotin-BSA |
| 2 | Anti-IgE | 2 | Mugwort |
| 3 | Milk | 3 | Ragweed, short |
| 4 | Egg White | 4 | *Alternaria alternata* |
| 5 | Crab | 5 | *Aspergillus fumigatus* |
| 6 | Shrimp | 6 | *Cladosporium herbarum* |
| 7 | Acacia | 7 | *Penicillium notatum* |
| 8 | Ash mix | 8 | Cat |
| 9 | Birch-alder mix | 9 | Dog |
| 10 | Sallow willow | 10 | Cockroach |
| 11 | Hazelnut | 11 | Housedust |
| 12 | Japanese cedar | 12 | *D. farinae* |
| 13 | Oak white | 13 | *D. pteronyssinus* |
| 14 | Poplar mix | 14 | Sweet vernal grass |
| 15 | Sycamore mix | 15 | Reed |
| 16 | Bermuda grass | 16 | Pine |
| 17 | Orchard grass | 17 | Oxeye daisy |
| 18 | Timothy grass | 18 | Japanese hop |
| 19 | Goldenrod | 19 | Mackerel |
| 20 | Rye pollens | 20 | Kiwi |
| 21 | Pigweed | 21 | Banana |
| 22 | Russian thistle | 22 | Apple |

300 μl of a test sample-diluted solution (PBS, 0.5% BSA) was put into plastic reaction wells, and 100 μl of a serum form an allergic patient was added thereto. Thereafter, the resulting mixture was reacted at room temperature while agitating for an hour. The solution in the reaction wells was discarded, and 0.4 ml of a washing solution (50 mm Tris, 0.2 M NaCl, 0.05% Tween 20) was divided into the reaction wells, and agitated at room temperature for 5 minutes, and the washing solution was removed. This procedure was additionally performed twice.

400 μl of a biotin-labeled anti-mouse human IgE solution was put into specimen-containing reaction wells, and agitated at room temperature. Biotin-labeled anti-mouse human IgE was prepared in the same manner as the biotin-labeled BSA described in Example 1. Thirty minutes after the reaction, the solution was discarded, and the reaction wells were washed with 400 μl of a washing solution while agitating at room temperature for 5 minutes, and the washing solution was then discarded. This procedure was performed twice, and 400 μl of a streptavidin-AP solution was put into the specimen-containing reaction wells, and agitated at room temperature. After 30 minutes, the solution was removed, the reaction wells were washed with 400 μl of a washing solution while agitating at room temperature for 5 minutes, and the washing solution was removed. This procedure was additionally performed twice to completely remove unattached streptavidin-AP. 400 μl of a colorimetric solution containing 0.2 mg/ml of bromochlorophenyl phosphate and 0.3 mg/ml of nitroblue tetrazolium was put into the specimen-containing reaction wells, and agitated at room temperature. After 20 minutes, the solution was removed, and the reaction wells were washed with 250 μl of distilled water. Then, the remaining solution was removed, and the reaction wells were then dried. As a result, it could be seen that the strips to which the allergens having specific IgE in the tested serum were attached turned black, as shown in FIG. 3. In this case, the color of the strips was able to be measured using a reader to quantify IgE in the specimen.

Example 3

Manufacture of Plastic Strip-Type Diagnostic Kit

As listed in Table 2, lines were drawn on four NC membranes (A, B, C and D) using solutions, in which different allergens and proteins were dissolved, in the same manner as in Example 1, and the markers were immobilized in the NC membranes. The NC membranes in which the allergens were immobilized were dried overnight at room temperature in a drying rack, and then attached to a plastic support. The NC membranes were cut at a distance of 1.5 mm in a longitudinal direction to manufacture strips. The cut pieces of the membrane A, the membrane B, the membrane C and the membrane D were attached to one plastic strip (FIG. 2).

TABLE 2

| Membrane A | | Membrane B | | Membrane C | | Membrane D | |
| --- | --- | --- | --- | --- | --- | --- | --- |
| Line | Marker | Line | Marker | Line | Marker | Line | Marker |
| 1 | Biotin-BSA | 1 | Biotin-BSA | 1 | Biotin-BSA | 1 | Biotin-BSA |
| 2 | Anti-IgE | 2 | Mugwort | 2 | Biotin-BSA | 2 | Mugwort |
| 3 | Milk | 3 | Ragweed, short | 3 | Anti-IgE | 3 | Ragweed, short |
| 4 | Egg white | 4 | *A. alternata* | 4 | Milk | 4 | *A. alternata* |
| 5 | Crab | 5 | *A. fumigatus* | 5 | Egg white | 5 | *A. fumigatus* |
| 6 | Shrimp | 6 | *C. herbarum* | 6 | Crab | 6 | *C. herbarum* |
| 7 | Acacia | 7 | *P. notatum* | 7 | Shrimp | 7 | Cat |
| 8 | Ash mix | 8 | Cat | 8 | Tuna | 8 | Dog |
| 9 | alder-Birch | 9 | Dog | 9 | Codfish | 9 | Cockroach |
| 10 | Sallow willow | 10 | Cockroach | 10 | Salmon | 10 | Housedust |
| 11 | Hazelnut | 11 | Housedust | 11 | Pork | 11 | *D. farinae* |
| 12 | Japanese cedar | 12 | *D. farinae* | 12 | Chicken | 12 | *D. pteronyssinus* |
| 13 | Oak white | 13 | *D. pteronyssinus* | 13 | Beef | 13 | Buck-wheat |
| 14 | Poplar mix | 14 | Sweet vernal grass | 14 | Wheat flour | 14 | *Candida albicans* |
| 15 | Sycamore mix | 15 | Reed | 15 | Rice | 15 | *Acarus siro* |
| 16 | Bermuda grass | 16 | Pine | 16 | Barely meal | 16 | Japanese hop |
| 17 | Orchard grass | 17 | Oxeye daisy | 17 | Garlic | 17 | Mackerel |
| 18 | Timothy grass | 18 | Japanese hop | 18 | Onion | 18 | PEA |
| 19 | Goldenrod | 19 | Mackerel | 19 | Peanut | 19 | Walnut |
| 20 | Rye pollens | 20 | Kiwi | 20 | Yeast, bakers | 20 | Anti-IgE 1 |
| 21 | Pigweed | 21 | Banana | 21 | Alder-Birch | 21 | Anti-IgE 2 |
| 22 | Russian thistle | 22 | Apple | 22 | Oak white | 22 | Anti-IgE 3 |
| | | | | 23 | Rye pollens | | |

A four-strip parallel line biochip was put into each reaction well, and 500 µl of a test sample-diluted solution (PBS, 0.5% BSA) was put into each plastic reaction well. Thereafter, 100 µl of a serum from an allergic patient was added to the reaction wells, and then reacted while agitating at room temperature for an hour. The solution in the reaction wells was discarded, 0.6 ml of a washing solution (50 mm Tris, 0.2 M NaCl, 0.05% Tween20) was divided into the reaction wells and agitated at room temperature for 5 minutes, and the washing solution was discarded. This procedure was additionally performed twice. 600 µl of a biotin-labeled anti-mouse human IgE solution was put into the specimen-containing reaction well, and agitated at room temperature. Biotin-labeled anti-mouse human IgE was prepared in the same manner as the biotin-labeled BSA described in Example 1. Thirty minutes after the reaction, the solution was discarded, and the reaction wells were washed with 400 µl of a washing solution while agitating at room temperature for 5 minutes, and the washing solution was then discarded. This procedure was performed twice, and 600 µl of a streptavidin-AP solution was put into the specimen-containing reaction wells, and agitated at room temperature. After 30 minutes, the solution was removed, and the reaction wells were washed with 600 µl of a washing solution while agitating at room temperature for 5 minutes, and the washing solution was removed. This procedure was additionally performed twice to completely remove unattached streptavidin-AP. 600 µl of a colorimetric solution containing 0.2 mg/ml of bromochlorophenyl phosphate and 0.3 mg/ml of nitroblue tetrazolium was put into the specimen-containing reaction wells, and agitated at room temperature. After 20 minutes, the solution was removed, and the reaction wells were washed with 600 µl, of distilled water. Then, the strips were taken out from the reaction wells, and dried (FIG. 3). As a result, it could be seen that the strips to which the allergen having specific IgE in the tested serum was attached turned black.

From the results, it was confirmed that the parallel line biochip according to the present invention in which a plurality of strips were disposed in parallel was able to be used, which made it possible to detect materials for many markers.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF MAJOR PARTS IN THE DRAWINGS

10: line strip
20: well
30: marker

INDUSTRIAL APPLICABILITY

A conventional line strip biochip has problems in that a large amount of a specimen is consumed, and a cycle of processes including introducing respective reaction solutions for biochips, allowing the biochips to react with materials and washing the biochips should be repeatedly performed. However, a parallel line biochip for multiplex diagnosis provided in the present invention has an advantage in that 40 or more materials may be analyzed since one parallel strip is prepared by minimizing individual line strips, disposing the plurality of line strips in parallel.

The invention claimed is:

1. A parallel line biochip for multiplex diagnosis comprising a plurality of line strips attached in parallel to a planar support removably immobilized within a reaction well such that the plurality of line strips are configured to be completely immersible in at least one sample solution, wherein each of the line strips comprises a different plurality of lines of markers, wherein each of the line strips has a width between a range of about 0.5 mm to 25 mm, and wherein the biochip has 22 or more lines of markers in total.

2. The parallel line biochip of claim 1, wherein the line strips are prepared by coating a membrane onto the planar support.

3. The parallel line biochip of claim 2, wherein the membrane is selected from the group consisting of nitrocellulose, nylon, polyvinylidene fluoride (PVDF), glass, and a plastic.

4. The parallel line biochip of claim 1, wherein the marker is selected from the group consisting of a protein, an antigen, an antibody, DNA, RNA, PNA, a drug, a chemical substance, and an aptamer.

5. A parallel line biochip for multiplex diagnosis comprising:
a plurality of line strips, each line strip formed by a membrane having a length and a width wholly adhered to a planar support removably immobilized to a reaction well; and
a plurality of linear marker regions positioned on each line strip, each linear marker region spanning the width of each line strip;
wherein the plurality of line strips are positioned in parallel alignment on the planar support;
wherein the plurality of linear marker regions are positioned in parallel alignment on each line strip; and
wherein each of the line strips comprises a different plurality of linear marker regions.

* * * * *